United States Patent [19]

Masaoka et al.

[11] Patent Number: 4,954,621

[45] Date of Patent: Sep. 4, 1990

[54] PROCESS FOR PRODUCING SUCROSE FATTY ACID POLYESTER

[75] Inventors: Kazuhiko Masaoka, Suzuka; Yukio Kasori, Yokkaichi, both of Japan

[73] Assignee: Mitsubushi Kasei Corporation, Japan

[21] Appl. No.: 362,275

[22] Filed: Jun. 6, 1989

[30] Foreign Application Priority Data

Jun. 14, 1988 [JP] Japan ................. 63-144743
Jun. 14, 1988 [JP] Japan ................. 63-144744
Jun. 14, 1988 [JP] Japan ................. 63-144745

[51] Int. Cl.$^5$ ............ C07H 13/00; C07H 1/00; B01J 20/00

[52] U.S. Cl. .................. 536/119; 536/115; 536/124; 536/127; 536/120; 502/80; 502/84; 502/85; 502/400; 502/407

[58] Field of Search ............ 536/119, 115, 127, 124, 536/120; 502/80, 81, 85, 400, 407

[56] References Cited

U.S. PATENT DOCUMENTS

| 2,812,324 | 11/1957 | Huber et al. | 536/119 |
| 2,831,854 | 4/1958 | Tucker et al. | 536/119 |
| 3,963,699 | 6/1976 | Rizzi et al. | 536/119 |
| 3,963,789 | 6/1976 | Kruse et al. | 502/84 |
| 4,072,628 | 2/1978 | Kruse et al. | 502/27 |
| 4,517,360 | 5/1985 | Volpenhein | 536/119 |
| 4,611,055 | 9/1986 | Yamamoto et al. | 536/119 |

FOREIGN PATENT DOCUMENTS 62-215598 9/1987 Japan.

Primary Examiner—Ronald W. Griffin
Assistant Examiner—Everett White
Attorney, Agent, or Firm—Jordan B. Bierman

[57] ABSTRACT

A process for producing a sucrose fatty acid polyester comprises reacting sucrose with fatty acid lower alcohol ester(s) in a solvent in the presence of an alkaline catalyst, wherein said fatty acid lower alcohol ester(s) are employed in an amount at least 5 times by mol as much as said sucrose. The alkaline catalyst component is removed from the reaction product thus obtained and the obtained sucrose fatty acid polyester-containing solution is catalytically treated with activated clay. This process enables the production of a sucrose fatty acid polyester containing an extremely small amount of ash components and having an extremely low color value. The alkaline catalyst used in this process may be recovered and reused, which further makes the process of the present invention advantageous.

10 Claims, No Drawings

PROCESS FOR PRODUCING SUCROSE FATTY ACID POLYESTER

FIELD OF THE INVENTION

This invention relates to a process for producing a sucrose fatty acid polyester. More particularly, it relates to a process for producing a sucrose fatty acid polyester containing an extremely small amount of ash component including alkaline metal compounds.

Sucrose is a polyhydric alcohol having eight hydroxyl groups per molecule. Thus sucrose fatty acid polyester include eight ester types depending on the number of substituting fatty acids per molecule, which is hereinafter referred to as "degree of substitution".

Sucrose fatty acid esters having an average number of substituting fatty acids per molecule, which is hereinafter referred to as "average substitution degree", of 4 or above are useful as, for example, an improving agent for fats and oils, an inhibitor for the absorption of cholesterol or an emulsifier for the preparation of an emulsion.

BACKGROUND OF THE INVENTION

Known processes for producing sucrose fatty acid polyesters include a microemulsion method (a solvent-free method) and a solvent method.

In the microemulsion method wherein an alkaline soap is used as a melting agent, a large amount of an alkaline catalyst, compared with the starting sucrose, is added in order to proceed the reaction. However this method is disadvantageous in that the addition of such a large amount of an alkaline catalyst would induce a side reaction between a fatty acid alcohol ester and the alkaline catalyst to thereby form a large amount of a soap, in addition to the desired transesterification products. This reaction should be essentially carried out at a high temperature, which causes the above-mentioned problem. The high reaction temperature further causes a serious coloration of the sucrose fatty acid polyester products.

In contrast thereto, the solvent method comprises reacting sucrose with a fatty acid lower alcohol ester(s) several times by mol as much as said sucrose in a solvent in the presence of a catalyst. In this case, the reaction can be conducted in the solvent under mild conditions and thus the obtained sucrose fatty acid polyester is superior in qualities to the one produced by the solvent-free method.

The solvent method enables the production of a sucrose fatty acid polyester of relatively excellent qualities. In particular, the sucrose fatty acid polyester product obtained by the solvent method contains less alkaline metal components such as fatty acid alkaline soaps than the one obtained by the solvent-free method does. However there has been known no method for economically removing a small amount of the alkaline metal components contained in the former product.

Even in the case of the solvent method, it is required to use a decolorizer in order to give a sucrose fatty acid polyester having a low color value and excellent qualities, which brings about some industrial problems such as a decrease in the yield of the product.

Furthermore, there has been known no method for recovering and reusing the alkaline catalyst in the production of a sucrose fatty acid polyester by the solvent method.

SUMMARY OF THE INVENTION

It is an object of the present invention to provide a process for readily producing a sucrose fatty acid polyester containing an extremely small amount of ash components such as alkaline metal compounds by a solvent method.

Further, it is another object of the present invention to provide a process for readily producing a sucrose fatty acid polyester having an extremely low color value by using an inexpensive adsorbent.

Furthermore, it is another object of the present invention to provide a process for advantageously producing a sucrose fatty acid polyester on an industrial scale by recovering an alkaline catalyst from the reaction product and reusing the same.

DETAILED DESCRIPTION OF THE INVENTION

Accordingly, the gist of the present invention resides in a process for producing a sucrose fatty acid polyester which comprises reacting sucrose with fatty acid lower alcohol ester(s) in a solvent in the presence of an alkaline catalyst, wherein said fatty acid lower alcohol esters are used in an amount at least 5 times by mol as much as said sucrose; said alkaline catalyst is removed from the reaction product; and the sucrose fatty acid polyester-containing solution thus obtained is catalytically treated with activated clay.

The sucrose fatty acid polyester produced by the process of the present invention includes those having an average substitution degree of fatty acids per molecule of at least 4.

Examples of the fatty acid lower alcohol ester to be used in the present invention include esters of fatty acids, for example, saturated fatty acids such as caproic acid, caprylic acid, capric acid, lauric acid, myristic acid, stearic acid and behenic acid and unsaturated fatty acids such as linolic acid, oleic acid and linolenic acid, among which saturated or unsaturated fatty acids having 12 to 22 carbon atoms are preferable; with lower alcohols such as methanol, ethanol, propanol and butanol. Either one of these fatty acid lower alcohol esters or a mixture thereof may be used in the present invention. These fatty acid lower alcohol ester(s) are employed in an amount at least 5, preferably 5 to 30, times by mol as much as the sucrose.

Examples of the solvent to be used in the present invention include tertiary amines such as trimethylamine, triethylamine, N-methylmorpholine, pyridine, quinoline, pyrazine, methylpyrazine and N,N-dimethylpiperidine; amide such as formamide, N,N-dimethylformamide, 2-pyrrolidone and N-methyl-2-pyrrolidone; and dialkyl sulfoxide such as dimethyl sulfoxide. Among these solvents, dimethyl sulfoxide is particularly preferable from the viewpoints of, for example, heat stability, dissolving capability for sucrose, safety and the separation of the reaction product upon the treatment of the same with activated clay after distilling off the solvent from the upper phase solution obtained by separating the reaction product. It is enough to use the solvent in an amount of 5 to 50% by weight based on the total amount of the starting sucrose and fatty acid lower alcohol(s).

Examples of the alkaline catalyst to be used in the present invention include alkaline metal hydroxides and alkaline metal salts of weak acids. In particular, alkaline metal carbonates such as potassium carbonate are preferable therefor. The catalyst may be usually employed in an amount of 0.001 to 0.1 time by mol, preferably 0.005 to 0.5 time by mol, as much as the fatty acid lower alcohol ester(s).

The process of the present invention may be carried out in various forms. A typical example thereof comprises the following steps 1 to 4.

Step 1:

In this step, sucrose is reacted with fatty acid lower alcohol ester(s) in the presence of an alkaline catalyst and a solvent at a temperature of 50° C. to 120° C. under pressure of 5 to 80 mmHg or under cooling, condensing and refluxing a solvent vapor under pressure conditions allowing the solvent to boil. Although a fresh alkaline catalyst is to be employed in the first reaction, a catalyst comprising solid matters recovered from the reaction product may be employed thereafter optionally together with a required amount of a fresh one.

For example, sucrose is fed into a reactor together with a solvent and then heated. The vapor is then cooled, condensed and refluxed while some portion thereof is distilled off to thereby dehydrate the solution in the system until the moisture content reaches 0.1% or less. Subsequently an alkaline catalyst, which may be the solid matters recovered from the reaction product as described above, and fatty acid lower alcohol ester(s) are fed into the system. The fatty acid lower alcohol ester(s) may be added either at once, dividedly or continuously. As described above, the system is maintained at a temperature of 50° C. to 120° C. and under pressure of 5 to 80 mmHg or under such pressure conditions as to allow the solvent to boil under the condition comprising cooling, condensing and refluxing the solvent vapor.

These starting materials may be fed at the following ratio. Namely, the fatty acid lower alcohol ester(s) may be used in an amount of 5 times by mol, preferably 30 times by mol, as much as sucrose.

The catalyst may be used, as an alkaline catalyst compound, usually in an amount of 0.001 to 0.1 time by mol, preferably 0.005 to 0.05 time by mol, as much as the fatty acid lower alcohol ester(s).

The reaction may usually conducted for 2 to 8 hours, preferably 4 to 6 hours.

In the step 1, the boiled solvent is to be cooled, condensed and then refluxed within the reaction system, while the lower alcohols formed by the reaction is to be distilled off. It is desirable that the reaction in this step 1 is continued until the average substitution degree reaches 5 or above. When the reaction is continuted to reach the abovementioned degree, the reaction system would become homogeneous or heterogeneous, depending on the feeding method of the fatty acid lower alcohol ester(s) as well as on an amount of the same, without containing any unreacted sucrose.

Steps 2 and 3 (or steps 2' and 3'):

In the present invention, the solvent may be disitlled off from the reaction product obtained in the above step 1 and then the residue may be subjected to solid/liquid separation at a temperature of 60° C. or above. Alternately, the reaction product obtained in the above step 1 may be separated and the solvent may be distilled off from the upper phase solution thus obtained.

Step 2:

The reaction product obtained in the step 1 is heated to thereby distill off the solvent. The heating may be preferably conducted under pressure of 30 to 5 mmHg at a temperature of 80° to 120° C. for 1 to 2 hours. After distilling off the solvent, the obtained product may be further heated to 130° to 180° C. under pressure of 5 mmHg or below preferably for 1 to 3 hours.

Step 3:

In this step, the catalyst is recovered from the reaction product obtained in the step 2 and simultaneously the aimed product, i.e., sucrose fatty acid polyester is obtained. Namely, the reaction product obtained in the step 2 is subjected to solid/liquid separation at a temperature of 60° C. or above, preferably 130° to 180° C., to thereby recover the solid matters comprising the catalyst. Altough the solid/liquid separation is usually conducted by filtering or centrifuging, other procedures may be employed therefor. The solid matters separated at this stage mainly comprise the alkaline catalyst residue. Therefore the reaction product, for example, the filtrate from which the solid matters have been removed contains a considerably lowered amount of alkaline metal components.

Step 2':

In this step, the reaction product obtained in the step 1 is allowed to stand. Thus the product separates into two phases. That is to say, the upper phase comprises a sucrose fatty acid polyester-containing solution while the lower one comprises a solution containing the alkaline catalyst component and colored matters. After removing the lower phase solution, the sucrose fatty acid polyester-containing solution is obtained.

Prior to the standing, the reaction product may be maintained at 60° to 120° C. and filtered or centrifuged to thereby remove solid matters therefrom. The standing may be preferably continued for 10 to 60 minutes.

Step 3':

The sucrose fatty acid polyester-containing solution obtained in the step 2' is heated to thereby remove the solvent. The heating may be preferably conducted under reduced pressure of 30 to 5 mmHg at 80° to 120° C. for 1 to 2 hours.

Step 4:

In this step, the sucrose fatty acid polyester-containing solution obtained in the above step 3 or 3' is catalytically treated with activated clay. The catalytic treatment may be conducted in various forms. The treating temperature may usually range from 60° to 180° C. while the treating period may usually range from 10 to 60 minutes. The activated clay may be employed in an amount of 1 to 30% by weight based on the reaction product from which the solid matters have been removed. The catalytic treatment may be conducted by mixing the sucrose fatty acid polyester-containing solution with the activated clay and stirring. Alternately, the sucrose fatty acid polyester-containing solution may be passed through a fixed bed of activated clay. This catalytic treatment may be preferably conducted in an inert gas atmosphere, such as nitrogen atmosphere, under reduced pressure.

After the completion of the catalytic treatment in the step 4, sucrose fatty acid polyester-containing solution may be, for example, centrifuged to thereby remove the activated clay. Thus the aimed sucrose fatty acid polyester can be obtained as such, though it may be further purified by, for example, molecular distillation, if required. Alternately, the purification such as molecular distillation may be conducted prior to the catalytic treatment with activated clay, namely, between the abovementioned step 3 or 3' and step 4.

The solid matters recovered by the solid/liquid separation in the above step 3 may be reused as the alkaline catalyst in the step 1. However it is preferable to wash said solid matters with a solvent prior to the use as the alkaline catalyst. The washing may be conducted with, for example, toluene, n-hexane, tetrahydrofuran of acetone. Among these washing liquors, n hexane and tetrahydrofuran are particularly preferable.

The most important characteristic of the present invention is to catalytically treat the reaction product, from which the alkaline catalyst component has been removed, with activated clay.

The removed alkaline catalyst component contains the alkaline catalyst residue as the main component. Thus the alkaline metal content in the reaction product can be considerably lowered thereby. Furthermore, ash components including the remaining alkaline metal compounds in the reaction product can be effectively removed by catalytically treating said reaction product, from which the alkaline catalyst component has been removed, with activated clay. In addition, the color value of the reaction product can be decreased thereby.

Activated clay is a clay adsorbent which is prepared by treating clay comprising montmorrilonite as the main component with an acid. It is considerably inexpensive, compared with other adsorbents such as activated carbon or ion exchange resins. Therefore the process of the present invention is further preferable from an economical viewpoint.

The treatment with activated clay may be usually conducted at a temperature of 60° to 180° C.

It is another characteristic of the process of the present invention that the reaction product is subjected to solid/liquid separation at a temperature of 60° C. or above and the solid matters thus recovered can be reused as the alkaline catalyst. When the reaction is to be carried out batchwise, for example, the solid matters recovered from the reaction products obtained by the previous reaction(s) may be reused. When the reaction is to be continuously conducted, on the other hand, the solid matters, which are recovered either batchwise or continuously in the above-mentioned later stage may be circulated and reused in the reaction system. In this case, the recovered solid matters may be used alone as the alkaline catalyst. Alternately, a fresh alkaline catalyst may be added thereto and the mixture may be used in the reaction, when the amount of the recovered solid matters does not satisfy the required catalytic level.

According to the process of the present invention, a highly pure sucrose fatty acid polyester containing an extremely small amount of alkaline metal components can be readily obtained and a sucrose fatty acid polyester having an extremely low color value can be obtained by using an inexpensive adsorbent.

Furthermore, the process of the present invention enables the recovery and reuse of an alkaline catalyst to thereby save the amount of said catalyst. In addition, the labor and cost for treating the waste alkaline catalyst can be saved thereby.

To further illustrate the present invention, and not by way of limitation, the following Examples will be given.

EXAMPLE 1

Step 1:

968.8 g of sucrose and 4500 g of a solvent (dimethyl sulfoxide, which will be called DMSO hereinafter) were fed into a thoroughly dried 30 l reactor provided with a stirrer. The solvent was boiled under pressure of 20 mmHg and the solvent vapor was cooled, condensed and refluxed. After 20 minutes, some portion of the solvent was distilled off to thereby dehydrate the content of the system. When the amount of the distilled DMSO reached 500 g, the distillation was ceased and the moisture in the system was determined. The moisture content thus determined was 0.06% by weight.

Subsequently, 92.1 g of anhydrous potassium carbonate, 4163 g of methyl stearate, 1878 g of methyl palmitate, 1954 g of methyl oleate and 1444 g of methyl linolate were added thereto. The DMSO was boiled under 20 mmHg while the vapor was cooled, condensed and refluxed. Simultaneously the methanol thus formed was distilled off. Thus the reaction was continued for 5 hours. The average reaction temperature was 90° C.

The reaction product was analyzed by high-performance liquid chromatgraphy under the conditions specified in Table 1. As a result, the obtained sucrose fatty acid polyester had the composition shown in Table 2. Namely, neither any sucrose fatty acid monoester to tetraester nor sucrose was detected.

TABLE 1

| | |
|---|---|
| HPLC device | Mfd. by Toyo Soda Mfg. Co., Ltd. Eluent-supply pump: CCPM Column thermostat: Co 8000, 50° C. |
| Separation column | Mfd. by Mitsubishi Chem. Ind., Ltd. OTS-1U, 4.6 mm (i.d.) × 250 mm (l.) 50° C. |
| Detector | Mfd. by British ACS Co. Mass detector 750-14 type Evaporator, 50° C. Nebulizer gas, $N_2$, 20 psi |
| Sample | Poured: 20 ml Conc.: 0.5% by vol (THF/toluene/methanol = 1/1/1.5) |
| Eluent | Flow rate: 1.5 ml/min Gradient condition: volume |

| Time (min) | 0 | 5 | 30 | 35 |
|---|---|---|---|---|
| THF | 1 | 1 | 30 | 30 |
| toluene | 1 | 1 | 30 | 30 |
| methanol | 98 | 98 | 40 | 40 |

Note: THF means tetrahydrofuran.

TABLE 2

| Sucrose fatty acid ester composition | (area %) |
|---|---|
| Pentaester | 11.6% |
| Hexaester | 29.1% |
| Heptaester | 39.3% |
| Octaester | 19.9% |
| Average substitution degree | 6.7 |

Step 2':

The above reaction product was maintained at 90° C. and filtered under elevated pressure by using a 10 l pressure filter provided with a jacket. At this stage, a filter paper having a retaining particle size of 1.0 μm was used and the pressure was elevated by using a nitrogen gas of 1.5 kg/cm² in pressure. 1.5 kg of the filtrate was introduced into a 2 l separation funnel provided with a jacket and allowed to stand at 90° C. for 30 minutes. Thus it separated into a lower phase solution containing colored matters and an upper phase solution containing the sucrose fatty acid polyester.

The DMSO and fatty acid methyl esters in the lower phase solution and upper phase solution were analyzed by gas chromatography. Table 3 shows the distribution rates thus determined.

TABLE 3

| | Lower phase solution (% by wt.) | Upper phase solution (% by wt.) |
|---|---|---|
| DMSO | 84 | 16 |

TABLE 3-continued

| | Lower phase solution (% by wt.) | Upper phase solution (% by wt.) |
|---|---|---|
| Fatty acid methyl eater | 6 | 94 |

Step 3':

Subsequently the upper phase solution separated from the lower phase solution was concentrated by vacuum evaporation until the boiling point thereof reached 155° C. under 1 Torr. Further it was treated with a down-flow film type molecular distillator MS-300 (mfd. by Shibata Kagaku K. K.) at a distillation tower wall temperature of 160° to 180° C. under pressure of 0.04 to 0.01 Torr at a feeding rate of 180 to 200 g/hr twice. Thus the content of the remaining fatty acid methyl esters was lowered to 0.02% by weight.

The color value, which is defined as follows, of the obtained sucrose fatty acid polyester was 24.2.

$$\text{Color value} = (2 - \log T)/(l \times c)$$

wherein l represents the thickness (cm) of the liquid layer in the cell used in the determination; C represents the amount (g) of the sample contained in 1 ml of the test solution; and T represents the transmittance at 420 nm.

The wavelength at which the above color value was determined, i.e., 420 nm was selected in order to show the degree of coloration, in particular, in a yellow color of the product. The coloration of the product would decrease with a decrease in this color value.

The obtained sucrose fatty acid polyester contained 0.9 mg equivalent/100 g of potassium and 0.09% by weight of ash.

Step 4:

1500 g of the sucrose fatty acid polyester obtained in the above step 3' was introduced into an activated clay-mixer which had an internal volume of 2 l and was provided with a stirrer and a jacket. The atmosphere in the mixer was substituted with a nitrogen gas and the temperature within the same was maintained at 90° C. Next, 46 g of activated clay SK-1 (mfd. by Nippon Kassei Hakudo K.K.) was added thereto and the resulting mixture was stirred for 30 minutes. After the completion of the catalytic treatment, the reaction mixture was filtered by using a 10 l pressure filter containing a filter paper of retaining particle size of 1.0 μm. The filtrate contained 0.1 mg equivalent/100 g or less of potassium and 0.01% by weight of ash. In addition, it was observed that this treatment with the activated clay further lowered the color value.

COMPARATIVE EXAMPLE 1

The reaction mixture obtained in the same manner as the one described in Example 1 was not separated but concentrated as such. The color value of the obtained concentrate measured in the same manner as the one described in Example 1 was 5.58.

EXAMPLE 2

Step 1:

968.8 g of sucrose and 4500 g of a solvent (DMSO) were fed into a thoroughly dried 30 l reactor provided with a stirrer. The solvent was boiled under pressure of 20 mmHg and the solvent vapor was cooled, condensed and refluxed. After 20 minutes, some portion of the solvent was distilled off to thereby dehydrate the content of the system. When the amount of the distilled DMSO reached 500 g, the distillation was ceased and the moisture in the system was determined. The moisture content thus determined was 0.06% by weight.

Subsequently, 92.1 g of anhydrous potassium carbonate, 4163 g of methyl stearate, 1878 g of methyl palmitate, 1954 g of methyl oleate and 1444 g of methyl linolate were added thereto. The DMSO was boiled under pressure of 20 mmHg while the vapor was cooled, condensed and refluxed. Simultaneously the methanol thus formed was distilled off. Thus the reaction was continued for 5 hours. The average reaction temperature was 90° C.

The reaction product was analyzed by high-performance liquid chromatgraphy under the same conditions as those specified in Table 1. As a result, the obtained sucrose fatty acid polyester had the composition shown in Table 4. Namely, neither any sucrose fatty acid monoester to tetraester nor sucrose was detected.

TABLE 4

| Sucrose fatty acid ester composition | (area %) |
|---|---|
| Pentaester | 11.6% |
| Hexaester | 29.1% |
| Heptaester | 39.3% |
| Octaester | 19.9% |
| Average substitution degree | 6.7 |

Step 2':

The above reaction product was heated from 90° C. to 150° C. within 60 minutes under pressure of 20 mmHg. During this period, the DMSO and formed methanol were distilled off from the system. When the temperature reached 150° C., the product was allowed to react at this temperature for 2 hours while maintaining the pressure to 3 to 4 mmHg.

The reaction product thus obtained was analyzed in the same manner as the one described in the step 1. Table 5 shows the results. Namely, no monoester to tetraester were formed. Furthermore, the DMSO concentration determined by gas chromatography with the use of an FPD detector was 33 ppm.

TABLE 5

| Sucrose fatty acid ester composition | (area %) |
|---|---|
| Pentaester | 6.1% |
| Hexaester | 16.0% |
| Heptaester | 24.6% |
| Octaester | 53.4% |
| Average substitution degree | 7.3 |

Step 3:

The reaction product obtained in the step 2 was filtered by using a 10 l pressure filter provided with a jacket at 70° to 80° C. under elevating the pressure with a nitrogen gas. At this stage, a filter paper having a retaining particle size of 1.0 μm was used while the elevated nitrogen gas pressure was 1.5 kg/cm². The filtrate contained 0.9 mg equivalent per 100 g of potassium and 0.09% by weight of ash.

Step 4:

1500 g of the filtrate obtained in the above step 3 was introduced into an activated clay-mixer which had an internal volume of 2 l and was provided with a stirrer and a jacket. The atmosphere in the mixer was substituted with a nitrogen gas and the temperature within the same was maintained at 90° C. Next, 167 g of activated clay SK-1 (mfd. by Nippon Kassei Hakudo K.K.)

was added thereto and the resulting mixture was stirred for 30 minutes. After the completion of the catalytic treatment, the reaction mixture was filtered by using a 10 l pressure filter containing a filter paper of a retaining particle size of 1.0 μm. The filtrate contained 0.1 mg equivalent per 100 g or less of potassium and 0.01% by weight of ash. In addition, it was observed that this treatment with the activated clay further lowered the color value.

Subsequently the filtrate was treated with a downflow film type molecular distillator MS-300 (mfd. by Shibata Kagaku K.K.) at a distillation tower wall temperature of 160° to 180° C. under pressure of 0.04 to 0.01 Torr at a feeding rate of 180 to 200 g/hr twice. Thus a highly pure sucrose fatty acid polyester containing 0.02% by weight of the remaining fatty acid methyl esters was obtained.

EXAMPLE 3

Step 3:

A reaction product obtained in the same manner described in the steps 1 and 2 was filtered through a 10 l pressure filter provided with a jacket under nitrogen gas-elevated pressure. At this stage, a filter paper having a retaining particle size of 1.0 μm was used while the nitrogen gas pressure was 1.5 kg/cm². The filtrate contained 0.9 mg equivalent per 100 g of potassium and 0.09% by weight of ash.

Subsequently the filtrate was treated with a downflow film type molecule distillator under the same conditions as those specified in Example 2. As a result, the content of the remaining fatty acid methyl esters became 0.03% by weight.

Step 4:

Next, 1500 g of the product from the molecule distillation was introduced into a 2 l activated claymixer provided with a stirrer and a jacket and 167 g of the same activated clay as the one used in Example 2 was added thereto. Then the activated clay treatment was conducted in the same manner as the one described in Example 2. After filtering, a highly pure sucrose fatty acid polyester containing 0.1 mg equivalent per 100 g or less of potassium and 0.01% by weight of ash was obtained.

COMPARATIVE EXAMPLE 2

The procedure of Example 3 was repeated except that no activated clay-treatment (step 4) was conducted. As a result, a sucrose fatty acid polyester containing 1.5 mg equivalent per 100 g of potassium and 0.15% by weight of ash was obtained.

EXAMPLE 4

Step 1:

968 8 g of sucrose and 4500 g of a solvent (DMSO) were fed into a thoroughly dried 30 l reactor provided with a stirrer. The solvent was boiled under pressure of 20 mmHg and the solvent vapor was cooled, condensed and refluxed. After 20 minutes, some portion of the solvent was distilled off to thereby dehydrate the system. When the amount of the distilled DMSO reached 500 g, the distillation was ceased and the moisture in the content of the system was determined. Thus the moisture content was 0.06% by weight.

Subsequently, 92.1 g of anhydrous potassium carbonate, 4163 g of methyl stearate, 1878 g of methyl palmitate, 1954 g of methyl oleate and 1444 g of methyl linolate were added thereto. The DMSO was boiled under pressure of 20 mmHg while the vapor was cooled, condensed and refluxed. Simultaneously the methanol thus formed was distilled off. Thus the reaction was continued for 5 hours. The average reaction temperature was 90° C.

The reaction product was analyzed by high-performance liquid chromatography under the same conditions as those specified in Table 1. As a result, the obtained sucrose fatty acid polyester had the composition shown in Table 6. Namely, neither any sucrose fatty acid monoester to tetraester nor sucrose was detected.

TABLE 6

| Sucrose fatty acid ester composition | (area %) |
|---|---|
| Pentaester | 11.6% |
| Hexaester | 29.1% |
| Heptaester | 39.3% |
| Octaester | 19.9% |
| Average substitution degree | 6.7 |

Step 2':

The above reaction product was heated from 90° C. to 150° C. within 60 minutes under pressure of 20 mmHg. During this period, the DMSO and formed methanol were distilled off from the system. When the temperature reached 150° C., the product was allowed to react at this temperature for 2 hours while maintaining the pressure to 3 to 4 mmHg.

The reaction product thus obtained was analyzed in the same manner as the one described in the step 1. Table 7 shows the results. Namely, no monoester to tetraester were formed. Furthermore, the DMSO concentration determined by gas chromatography with the use of an FRD detector was 33 ppm.

TABLE 7

| Sucrose fatty acid ester composition | (area %) |
|---|---|
| Pentaester | 6.1% |
| Hexaester | 16.0% |
| Heptaester | 24.6% |
| Octaester | 53.4% |
| Average substitution degree | 7.3 |

Step 3:

The reaction product obtained in the above step 3 was pressure-filtered while maintaining at 70° to 80° C. to thereby recover 959 g of solid matters. The filtrate was employed as a product as such.

Reuse of the recovered solid matters:

11.4 g portion of the solid matters recoverd in the above step 3 (858 g in total), which corresponded to 17.7 mg equivalent in terms of K+, was used as such as a catalyst. 25.7 g of sucrose, 11.2 g of methyl stearate, 50.7 g of methyl palmitate, 52.7 g of methyl oleate, 39.0 g of methyl linolate and 150 g of DMSO were added thereto. The obtained mixture was fed into a 0.5 l reactor and treated in the same manner as the one described in the above steps 1 to 3.

The reaction product (filtrate) obtained after the separation of the solid matters obtained in the step 3 in this process wherein the recovered solid matters were reused was analyzed in the same manner as the one described in the above step 1. Table 8 shows the composition of the obtained sucrose fatty acid polyester. As Table 8 indicates, neither any monoester nor diester was formed.

TABLE 8

| Sucrose fatty acid ester composition | (area %) |
| --- | --- |
| Triester | 2.4% |
| Tetraester | 18.2% |
| Pentaester | 28.7% |
| Hexaester | 30.3% |
| Heptaester | 18.2% |
| Octaester | 2.2% |
| Average substitution degree | 5.5 |

EXAMPLE 2

The procedure described in the steps 1 to 3 in Example 4 was repeated. Subsequently the solid matters obtained after the solid/liquid separation in the step 3 were washed with n-hexane and then lyophilized to thereby give a white solid.

2.44 g of this white solid, corresponding to 35.4 mg equivalent in terms of $K^+$, was fed into a 0.5 l reactor as a catalyst. Then the process for the reuse of the recovered solid matters described in Example 4 was repeated except that the pressure was maintained at 1.2 mmHg after the temperature reached 150° C. in the step 2.

The reaction mixture obtained in the step 2 was analyzed in the same manner as the one described in Example 4. Table 9 shows the results. As Table 9 indicates, no mono- to pentaester was formed.

TABLE 9

| Sucrose fatty acid ester composition | (area %) |
| --- | --- |
| Hexaester | 6.2% |
| Heptaester | 26.8% |
| Octaester | 67.0% |
| Average substitution degree | 7.61 |

While the invention has been described in detail and with reference to specific examples thereof, it will be apparent to one skilled in the art that various changes and modifications can be made therein without departing from the spirit and scope thereof.

What is claimed is:

1. A process for producing a sucrose fatty acid polyester comprising reacting sucrose with fatty acid lower alcohol ester(s) in a solvent in the presence of an alkaline catalyst, wherein said fatty acid lower alcohol ester(s) are employed in an amount at least 5 times by mol as much as said sucrose; the alkaline catalyst component is removed from the reaction product thus obtained; and the obtained sucrose fatty acid polyester-containing solution is catalytically treated with activated clay.

2. A process for producing a sucrose fatty acid polyester as claimed in claim 1, wherein the solvent is distilled off from the reaction product; then said reaction product is subjected to solid/liquid separation; and the sucrose fatty acid polyester-containing solution thus obtained is catalytically treated with activated clay.

3. A process for producing sucrose fatty acid polyester as claimed in claim 1, wherein said reaction product is separated into an upper phase solution containing the sucrose fatty acid polyester and a lower phase solution containing the alkaline catalyst component; said lower phase solution is removed; the solvent is distilled off from said upper phase solution; and the sucrose fatty acid polyester-containing solution thus obtained is catalytically treated with activated clay.

4. A process for producing a sucrose fatty acid polyester as claimed in claim 1, wherein the alkaline catalyst component separated from the reaction product is reused in the subsequent reaction as the alkaline catalyst.

5. A process for producing a sucrose fatty acid polyester as claimed in claim 1, wherein said solvent is dimethyl sulfoxide.

6. A process for producing a sucrose fatty acid polyester as claimed in claim 1, wherein said sucrose fatty acid polyester-containing solution is catalytically treated with activated clay at a temperature of 60° to 180° C.

7. A process for producing a sucrose fatty acid polyester as claimed in claim 1, wherein said alkaline catalyst is an alkaline metal salt of a weak acid.

8. A process for producing a sucrose fatty acid polyester as claimed in claim 1, wherein the average number of substituting fatty acids of said sucrose fatty acid polyester is 4 to 8.

9. A process for producing a sucrose fatty acid polyester as claimed in claim 1, wherein the average number of substituting fatty acids of said sucrose fatty acid polyester is 7 to 9.

10. A process for producing a sucrose fatty acid polyester as claimed in claim 1, wherein methyl ester(s) of fatty acid(s) remaining in said sucrose fatty acid polyester-containing solution are removed by molecular distillation either before or after the catalytic treatment with activated clay.

* * * * *